US007067273B2

(12) United States Patent
Zhang et al.

(10) Patent No.: US 7,067,273 B2
(45) Date of Patent: Jun. 27, 2006

(54) PEPTIDE SUBSTRATES OF A PROTEOLYTIC ADAM33 POLYPEPTIDE AND ASSAYS USING THE SAME

(75) Inventors: Rumin Zhang, Edison, NJ (US); Jun Zou, Cranbury, NJ (US); Feng X. Zhu, Edison, NJ (US); James P. Durkin, Succasunna, NJ (US); William T. Windsor, East Brunswick, NJ (US); Shelby P. Umland, Boonton, NJ (US)

(73) Assignee: Schering Corporation, Kenilworth, NJ (US)

( * ) Notice: Subject to any disclaimer, the term of this patent is extended or adjusted under 35 U.S.C. 154(b) by 7 days.

(21) Appl. No.: 10/741,205

(22) Filed: Dec. 19, 2003

(65) Prior Publication Data

US 2004/0152869 A1 Aug. 5, 2004

Related U.S. Application Data

(60) Provisional application No. 60/440,263, filed on Jan. 15, 2003, provisional application No. 60/434,830, filed on Dec. 19, 2002, provisional application No. 60/434,802, filed on Dec. 19, 2002.

(51) Int. Cl.

| | |
|---|---|
| ***C07K 7/06*** | (2006.01) |
| ***C07K 7/08*** | (2006.01) |
| ***C12Q 1/37*** | (2006.01) |

(52) U.S. Cl. ........................ 435/23; 530/327; 530/328; 530/345

(58) Field of Classification Search ................ 530/300, 530/327, 328, 345; 514/2, 14, 15, 16; 435/23
See application file for complete search history.

(56) References Cited

OTHER PUBLICATIONS

Weiss and Raby, "Asthma genetics 2003," *Hum Mol Genet*, 13(Suppl 1):R83-R89 (2004); (Epub Feb. 5, 2004).
Powell et al., "The splicing and fate of ADAM33 transcripts in primary human airways fibroblasts," *Am J Respir Cell Mol Biol* (Epub Jan. 23, 2004).
Werner et al., "Asthma is associated with single-nucleotide polymorphismss in ADAM33," *Clin Exp Allergy*, 34(1):26-31 (2004).
Postma and Howard, "ADAM33 gene: confirming a gene without linkage," *Clin Exp Allergy*, 34(1):1-3 (2004).
Zou et al., "Catalytic activity of human ADAM33" *J Biol Chem*, 279(11):9818-9830 (2004); (Epub Dec. 15, 2003).
Orth et al., "Crystal structure of the catalytic domain of human ADAM33," *J Mol Biol*, 335(1):129-137 (2004).
Howard et al., "Association of a disintegrin and metalloprotease 33 (ADAM33) gene with asthma in ethnically diverse populations," *J Allergy Clin Immunol*, 112(4):717-722, 2003.
Umland et al., "Mouse ADAM33 : Two, splice variants differ in protein maturation and localization," *Am J Respir Cell Mol Biol*, 30(4):530-539 (2004); (Epub Sep. 11, 2003).
Lind et al., "ADAM33 is not associated with asthma in Puerto Rican or Mexican populations," *Am J Respir Crit Care Med*, 168(11):1312-1316 (2003); (Epub Sep. 4, 2003).
Powell et al., "ADAM33: a novel therapeutic target for asthma," *Expert Opin Ther Targets*, 7(4):485-494 (2003).
Demoly, "[Respiratory allergic disease genes]," *Rev Pneumol Clin*, 59(2 Pt 1):67-75 (2003) French.
Umland et al., "Human ADAM33 messenger RNA expression profile and post-transcriptional regulation," *Am J Respir Cell Mol Biol*, 29(5):571-582 (2003); (Epub May 30, 2003).
Chae et al., "Identification of novel polymorphisms in the ADAM33 gene," *J Hum Genet*, 48(5):278-281 (2003); (Epub Apr. 15, 2003).
Cookson, "A new gene for asthma: would you ADAM and Eve it?" *Trends Genet*, 19(4):169-172 (2003).
Davies et al., "Airway remodeling in asthma: new insights," *J Allergy Clin Immunol*, 111(2):215-225; quiz 226 (2003).
Garlisi et al., "Human ADAM33: protein maturation and localization," *Biochem Biophys Res Commun*, 301(1):35-43 (2003).
Ahmadi and Goldstein, "Multifactorial diseases: asthma genetics point the way," *Currr Biol*, 12(20):R702-R704 (2002).
Van Eerdewegh et al., "Association of the ADAM33 gene with asthma and bronchial hyperresponsiveness," *Nature*, 418(6896):426-430 (2002); ( Epub Jul. 10, 2002).
Gunn et al., "Identification and preliminary characterization of mouse ADAM33," *BMC Genet*, 3(1):2 (2002); ( Epub Feb. 13, 2002).
Yoshinaka et al., "Identification and characterization of novel mouse and human ADAM33s with potential metalloprotease activity," *Gene*, 282(1-2):227-236 (2002).

*Primary Examiner*—Jeffrey Edwin Russel

(57) ABSTRACT

The present invention discloses peptide substrates of a proteolytic ADAM33 polypeptide. The present invention also discloses methods of identifying additional substrates of a proteolytic ADAM33 polypeptide. Furthermore, the present invention discloses methods of identifying compounds that inhibit the proteolytic activity of a proteolytic ADAM33 polypeptide.

13 Claims, No Drawings

PEPTIDE SUBSTRATES OF A PROTEOLYTIC ADAM33 POLYPEPTIDE AND ASSAYS USING THE SAME

REFERENCE TO RELATED APPLICATIONS

This application claims the benefit of U.S. Provisional Applications 60/434,802 filed Dec. 19, 2002; 60/434,830 filed Dec. 19, 2002; and 60/440,263 filed Jan. 15, 2003.

All references cited herein are incorporated in their entirety by reference.

BACKGROUND OF THE INVENTION

1. Field of Invention

The present invention pertains to peptide substrates of a proteolytic ADAM33 polypeptide. In addition, the present invention pertains to identification of additional substrates of a proteolytic ADAM33 polypeptide. Furthermore, the present invention pertains to the use of these peptide substrates for identifying compounds that inhibit the proteolytic activity of a proteolytic ADAM33 polypeptide.

2. Background

Asthma is a chronic respiratory disorder that afflicts hundreds of millions of people throughout the world [Drazen and Weiss, *Nature*, 418(6896):383–384 (2002)]. Though the occurrence of this respiratory disorder has been noted for over two thousand years, during the past twenty years industrialized nations have experienced an increase in asthma sufferers that approaches epidemic proportions [Umetsu et al., *Nat Immunol*, 3(8):715–720 (2002)]. Indeed, 10–20% of the population of industrialized countries currently suffer from asthma. Not surprisingly, the dramatic increase in the number of asthmatics in industrialized nations has resulted in a concomitant expenditure of resources to treat this condition [Umetsu et al., *Nat Immunol*, 3(8):715–720 (2002)]. Despite this strong commitment, to date the treatments employed only control the symptoms.

Asthma is characterized by life-threatening attacks due to episodic obstructions to, or abnormal narrowing of the airways in response to otherwise innocuous stimuli [Drazen and Weiss, *Nature*, 418(6896):383–384 (2002)]. Common symptoms of asthma include recurrent episodes of coughing, wheezing and breathlessness. The immediate cause for the thickening of the airway walls, smooth muscle contraction, and narrowing of the airways observed in asthmatics is an inflammation mediated by T-cells [Van Eerdewegh et al., *Nature*, 418(6896):426–430 (2002)]. Both genetic and environmental factors play key roles in inducing this T-cell-mediated inflammation, though the actual mechanism has yet to be delineated. What is known is that asthmatics have a genetic predisposition for the disease, and environmental factors serve to either trigger or protect against this immunological dysregulation [Umetsu et al., *Nat Immunol*, 3(8):715–720 (2002)].

Recently, the gene encoding a membrane anchored protein known as ADAM33 has been shown to be linked to asthma by positional cloning in an outbred population [Van Eerdewegh et al., *Nature*, 418(6896):426–430 (2002)]. Both human and mouse ADAM33 have been identified and characterized [Yoshinaka et al., *Gene*, 282(1–2):227–236 (2002); Gunn et al., *BMC Genet*, 3(1):2, (2002)].

ADAM33, expressed primarily in human lung fibroblasts and bronchial smooth muscle [Van Eerdewegh et al., *Nature*, 418(6896):426–430 (2002)], is a member of the "A Disintegrin And Metalloprotease" (ADAM) family of proteins. The ADAM family of proteins comprises over thirty such proteins, including the well characterized TNF-alpha converting enzyme (TACE) [Cross et al., *J Am Chem Soc*, 124(37):11004–11007 (2002); Schlondorff and Blobel, *J Cell Sci*, 112(Pt 21):3603–3617 (1999); Black, *Int J Biochem Cell Biol*, 34(1):1–5 (2002); U.S. Pat. No. 5,830,742]. The ADAM family of proteins is a class of type-I transmembrane proteins that share a unique domain structure composed of a signal sequence, a prodomain, a metalloprotease/catalytic domain, a disintegrin domain, a cysteine-rich domain, an epidermal growth factor-like domain, a transmembrane and a cytoplasmic domain. Though, both human and mouse ADAM33 have been identified and sequenced, heretofore, little specific information has been provided regarding their catalytic activity. Moreover, the ADAM33 protein domains, including the catalytic domain, have not been specifically delineated and isolated.

Due to its genetic linkage to asthma and expression pattern, ADAM33 has become a promising target protein for use in identifying compounds to treat asthma [Shapiro and Owen, *N Engl J Med*, 347(12):936–938 (2002)]. Prior to this invention, no substrate of a proteolytic ADAM33 polypeptide had been identified. In particular, the identification of substrates of a proteolytic ADAM33 polypeptide is important for assaying its proteolytic activity. In addition, substrates of a proteolytic ADAM33 polypeptide would be useful for assaying compounds that modulate the proteolytic activity of a proteolytic ADAM33 polypeptide. In particular, compounds that inhibit the proteolytic activity of a proteolytic ADAM33 polypeptide may be useful in the treatment of asthma.

Therefore, there is a need for substrates of a proteolytic ADAM33 polypeptide. In addition, there is a need to provide methods for identifying compounds that are substrates of a proteolytic ADAM33 polypeptide. Furthermore, there is a need to provide methods for identifying compounds that inhibit the proteolytic activity of a proteolytic ADAM33 polypeptide.

SUMMARY OF THE INVENTION

The present invention provides peptide substrates of a proteolytic ADAM33 polypeptide. Such peptide substrates comprise an amino acid sequence designated as P5-P4-P3-P2-P1-P1'-P2'-P3'-P4' [following the notation of Schechter and Berger, *Biochem Biophys Res Comm*, 27(2):157–162 (1967)] wherein P5 is Trp, Tyr, Phe, Ile, Leu, Met, Val, or an analog thereof; P4 is Ala, Cys, Asp, Glu, Phe, His, Ile, Lys, Leu, Met, Asn, Pro, Gln, Arg, Ser, Thr, Val, Tyr, an analog thereof, or an amino acid derivative; P3 is Val, Ile, or an analog thereof; P2 is Ala, Met, Leu, Lys, Arg, His, or an analog thereof; P1 is Phe, Tyr, Met, His, Ala, Arg, Glu, Gln, Gly, Leu, Pro, Ser, Trp, or an analog thereof; P1' is Gln, Leu, Met, His, or an analog thereof; P2' is Ile, Val, Lys, Arg, Leu, Met, Phe, Tyr, Trp, or an analog thereof; P3' is Leu, Ile, Met, His, Trp, or an analog thereof; P4' is Trp, Ala, Ile, Leu, Met, Val, Phe, Tyr, Arg, His, Lys, or an analog thereof.

Methods for identifying whether a test compound is a substrate of a proteolytic ADAM33 polypeptide are also provided. Specifically, cleavage of the test compound by a proteolytic ADAM33 polypeptide is measured. Cleavage of the test compound indicates that the test compound is a substrate of the proteolytic ADAM33 polypeptide.

In addition, methods for identifying whether a test compound inhibits the proteolytic activity of a proteolytic ADAM33 polypeptide are provided. Specifically, cleavage of a substrate by a proteolytic ADAM33 polypeptide is measured in the presence and absence of a test compound.

A decrease in cleavage of the substrate in the presence of the test compound indicates that the test compound inhibits the proteolytic activity of the proteolytic ADAM33 polypeptide.

Accordingly, it is a principal object of the present invention to provide substrates of a proteolytic ADAM33 polypeptide.

It is a further object of the present invention to provide a method for identifying whether a test compound is a substrate of a proteolytic ADAM33 polypeptide.

It is a further object of the present invention to provide a method for identifying whether a test compound inhibits the proteolytic activity of a proteolytic ADAM33 polypeptide.

These and other aspects of the present invention will be better appreciated by reference to the following Detailed Description.

DETAILED DESCRIPTION OF THE INVENTION

The present invention provides peptide substrates of a proteolytic ADAM33 polypeptide, comprising the sequence designated as: P5-P4-P3-P2-P1-P1'-P2'-P3'-P4', wherein P5 is Trp, Tyr, Phe, Ile, Leu, Met, Val, or an analog thereof; P4 is Ala, Cys, Asp, Glu, Phe, His, Ile, Lys, Leu, Met, Asn, Pro, Gln, Arg, Ser, Thr, Val, Tyr, an analog thereof, or an amino acid derivative; P3 is Val, Ile, or an analog thereof; P2 is Ala, Met, Leu, Lys, Arg, His, or an analog thereof; P1 is Phe, Tyr, Met, His, Ala, Arg, Glu, Gln, Gly, Leu, Pro, Ser, Trp, or an analog thereof; P1' is Gln, Leu, Met, His, or an analog thereof; P2' is Ile, Val, Lys, Arg, Leu, Met, Phe, Tyr, Trp, or an analog thereof; P3' is Leu, Ile, Met, His, Trp, or an analog thereof; P4' is Trp, Ala, Ile, Leu, Met, Val, Phe, Tyr, Arg, His, Lys, or an analog thereof. Preferably, P5 is Trp, Tyr, Phe, or an analog thereof; P2 is Ala or an analog thereof; P1 is Phe, Tyr, Met, His, or an analog thereof; P1' is Gln or an analog thereof; P2' is Ile, Val, Lys, or an analog thereof; P3' is Leu or an analog thereof; or P4' is Trp, Ala, or an analog thereof. In a preferred embodiment, the peptide comprises 9 to 16 amino acid residues.

In a related embodiment, the present invention provides a peptide comprising the amino acid sequence set forth in SEQ ID NO: 1. Preferably, the peptide comprises the amino acid sequence set forth in SEQ ID NO: 2. More preferably, the peptide comprises the amino acid sequence set forth in SEQ ID NO: 3; SEQ ID NO: 4; SEQ ID NO: 5; or SEQ ID NO: 6.

In another embodiment, the present invention provides a peptide comprising the amino acid sequence set forth in SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; or SEQ ID NO: 12. Of note, the peptides described above may have one conservative amino acid substitution. In a related embodiment, the present invention provides a peptide comprising the amino acid sequence set forth in SEQ ID NO: 13.

In yet another embodiment, the peptides of the present invention may comprise a detectable moiety. The detectable moiety may be a fluorescent donor; an acceptor; a fluorophore; or a protein marker. The fluorescent donor may be selected from the group consisting of Edans, Mca, Cy3B, and Alexa Fluor 546. The acceptor may be selected from the group consisting of Alexa Fluor 647, Cy5, Dabcyl, Dnp, and Cy5Q. The fluorophore may be selected from the group consisting of fluorescein, rhodamine, Texas red, BODIPY derivatives, Alexa™ Fluor, and Cy™ dyes. The protein marker may be selected from the group consisting of biotin, digoxin, and phosphotyrosine. In a related embodiment, the present invention provides a peptide comprising: P5 through P5', wherein P4 is an amino acid derivative that comprises a fluorescent donor and P5' comprises an acceptor; or P4 is an amino acid derivative that comprises an acceptor and P5' comprises a fluorescent donor. The present invention also provides a peptide comprising P6 through P5', wherein P6 comprises a fluorescent donor and P5' comprises an acceptor; or P6 comprises an acceptor and P5' comprises a fluorescent donor. The peptide may be selected from the group consisting of SEQ ID NO: 14; SEQ ID NO: 15; SEQ ID NO: 16; SEQ ID NO: 17; and SEQ ID NO: 18. In addition, the present invention provides a peptide comprising P6 through P5', wherein P6 comprises a protein marker and P5' comprises a fluorophore; or P6 comprises a fluorophore and P5' comprises a protein marker.

In a related embodiment, the present invention provides a peptide selected from the group consisting of: SEQ ID NO: 19; SEQ ID NO: 20; and SEQ ID NO: 21.

The present invention provides a method for identifying whether a test compound is a substrate of a proteolytic ADAM33 polypeptide, comprising: contacting the proteolytic ADAM33 polypeptide with the test compound; and measuring cleavage of the test compound; wherein cleavage of the test compound indicates that the test compound is a substrate of the proteolytic ADAM33 polypeptide. The measuring step may be by means of a high throughput fluorescence device or a high performance liquid chromatography device.

In addition, the present invention provides a method for identifying whether a test compound inhibits proteolytic activity of a proteolytic ADAM33 polypeptide, comprising: contacting the proteolytic ADAM33 polypeptide with a substrate of the proteolytic ADAM33 polypeptide; measuring cleavage of the substrate; adding the test compound; measuring cleavage of the substrate in the presence of the test compound; wherein a decrease in cleavage of the substrate in the presence of the test compound indicates that the test compound inhibits the proteolytic activity of the proteolytic ADAM33 polypeptide. The substrate may be any of the peptides described herein. Furthermore, the measuring step may be by means of a high throughput fluorescence device or a high performance liquid chromatography device.

As used herein, in reference to amino acids, the term "analog" refers to a molecule that is structurally similar to a naturally occurring amino acid with molecular properties that are partially preserved. The following non-exclusive examples of modifications to naturally occurring amino acids that form amino acid analogs is illustrative and not meant to be limiting. Amino acid analogs may contain a modification in acetylation, methylation, phosphorylation, carboxylation, or glycosylation from that of a naturally occurring amino acid. Alternatively, amino acid analogs may contain a modification to one or more peptide bonds (e.g., by replacement with a non-peptide bond) that results in a more flexible bonds or more constrained bonds (e.g., cyclic amino acid analogs). Amino acid analogs may contain a modification that results in a change in charge. Amino acid analogs also include non-naturally occurring synthetic amino acids. Analogs of amino acids can be found in the Chemical Abstract database. In addition, analogs of amino acids can be found in on-line databases, including the Amino Acid Database. Likewise, analogs of amino acids can be found in hardprint catalogs from prevailing commercial suppliers of amino acid building blocks, such as NovaBiochem, Advanced ChemTech, PepTech, Neosystem, Bachem Biosciences, RSP Amino Acid Analogues. The following is an exemplary nonexclusive list of analogs for some specific amino acids.

Trp analogs include, but are not limited to, napththylalanine, nor-tryptophane, and benzothienylalanine.

Tyr/Phe analogs include, but are not limited to, homophenylalanine, cyclohexylalanine, phenylglycine, styrylalanine, furylalanine, thiazolylalanine, pyridylalanine, thienylalanine, halogen-substituted Phe, methyl-substituted Phe, cyano-substituted Phe, nitro-substituted Phe, amino-substituted Phe, tetrahydroisoquinoline-1-carboxylic acid and tetrahydroisoquinoline-3-carboxylic acid.

Ile, Leu, Met, Val analogs include, but are not limited to, aminobutyric acid, allylglycine, propargylglycine, S-methylcysteine, S-ethylcysteine, norvaline, norleucine, tert-leucine, and allo-isoleucine.

Ala analogs include, but are not limited to, beta-fluoroalanine, beta-chloroalanine, beta-cyanoalanine, and aminoisobutyric acid.

Lys/Arg analogs include, but are not limited to, diaminopropionic acid, diaminobutyric acid, ornithine, and citruline.

His analogs include, but are not limited to, furylalanine, thiazolylalanine, and thienylalanine.

As used herein, the term "conservative amino acid substitution" is the substitution of an amino acid residue of a peptide by a substitute amino acid residue where both the amino acid residue and the substitute amino acid residue are members of the same class selected from the group consisting of nonpolar amino acids, aromatic amino acids, polar neutral amino acids, positively charged amino acids and negatively charged amino acids.

As used herein, the term "detectable moiety" is a molecule whose presence can be assayed, for example, by spectroscopic, photochemical, biochemical, immunochemical, or chemical means. For example, the term detectable moiety includes, but is not limited to, fluorescent donors, acceptors, fluorophores and protein markers.

As used herein, the term "fluorescent donor" is a molecule that transfers energy to an acceptor molecule via long range dipole-dipole coupling. This process occurs because the transferred electron is less tightly bound to the donor in its excited state than it is in the ground state. For example, the term fluorescent donor includes, but is not limited to, Edans=5-[(2-aminoethyl)amino]naphthalene-1-sulfonic acid, Mca=(7-methoxycoumarin-4-yl)acetyl, Cy3B dye (Amersham Biosciences, NJ), and Alexa Fluor 546 dye (Molecular Probes, CA).

As used herein, the term "acceptor" is a molecule that accepts energy from an excited donor molecule via long range dipole-dipole coupling. For example, the term acceptor includes, but is not limited to, Alexa Fluor 647 (Molecular Probes, CA), Cy5 (Amersham Biosciences, NJ), Dabcyl=4-(4-dimethylaminophenyl-azo)benzoyl (Amersham Biosciences, NJ; e.g., a quencher for Edans), Dnp=2,4-dinitrophenyl (Amersham Biosciences, NJ; e.g., a quencher for Mca), and Cy5Q dye (Amersham Biosciences, NJ; e.g., a quencher for Cy3B).

As used herein, the term "fluorophore" is a molecule that contains a fluorescent group. For example, the term fluorophore includes, but is not limited to, fluorescein, rhodamine, Texas red, BODIPY derivatives, Alexa™ Fluor dyes (e.g., Alexa Fluor 568, Alexa Fluor 594, and Alexa Fluor 647), and Cy™ dyes (e.g., Cy3B and Cy5Q).

As used herein, the term "protein marker" is an amino acid derivative containing a low molecular weight moiety, preferably less than 1 kD capable of binding a high molecular weight molecule, preferably greater than 20 kD. For example, the term protein marker includes, but is not limited to, biotin, digoxin, and phosphotyrosine. In which case, the corresponding high molecular weight molecule may be avidin, anti-digoxin antibody, and anti-phosphotyrosine antibody, respectively.

As used herein, the term "fluorescence resonance energy transfer (FRET)" refers to a distance-dependent interaction between the electronic excited states of two fluorophores in which excitation is transferred from a fluorescent donor to an acceptor without emission and reabsorption of a photon. Primary conditions for FRET are as follows: i) donor and acceptor molecules must be in close proximity (typically 10–100 Å); ii) the absorption spectrum of the acceptor must overlap the fluorescence emission spectrum of the donor; and iii) donor and acceptor transition dipole orientations must be approximately parallel. The efficiency of FRET is dependent on the inverse sixth power of the intermolecular separation [Haugland, *Proc Natl Acad Sci USA*, 58(2): 719–726 (1967)] making it useful over distances comparable with the dimensions of biological macromolecules. Thus, FRET is an important technique for investigating a variety of biological phenomena that produce changes in molecular proximity. [See for example, dos Remedios and Moens, J Struct Biol, 115(2):175–185 (1995); Selvin, *Methods Enzymol*, 246:300–334 (1995); Boyde et al., *Scanning*, 17(2): 72–85 (1995); Wu and Brand, *Anal Biochem*, 218(1):1–13 (1994); dos Remedios et a., *J Muscle Res Cell Motil*, 8(2):97–117 (1987); Stryer, *Annu Rev Biochem*, 47:819–846 (1978); Fairclough and Cantor, *Methods Enzymol*, 48:347–379 (1978)].

As used herein, the term "fluorescent quenching (FQ)" refers to a bimolecular process which reduces the intensity of the fluorescence emission of a fluorophore. For example, quenching by small molecules either in a solvent or bound to a peptide in close proximity to a fluorophore can reduce the fluorescence quantum yield without changing the fluorescence emission spectrum. Quenching can result from transient excited-state interactions (collisional or dynamic quenching) or from formation of nonfluorescent ground-state species (static quenching; quenching by energy transfer or charge transfer reactions). The accessibility of groups on a peptide can be measured by use of quenchers to perturb fluorophores.

As used herein, the term "fluorescent polarization (FP)" refers to the emission of polarized light from an excited fluorescently-labeled molecule. When a fluorescent molecule is excited with plane polarized light it emits light in the same polarized plane provided that the molecule remains stationary throughout the excited state (e.g., 4 nanoseconds in the case of fluorescein). But, if the excited molecule rotates or tumbles out of the plane of polarized light during the excited state, then light is emitted in a different plane from that of the initial excitation. If vertically polarized light is used to excite the fluorophore, the emission light intensity can be monitored in both the original vertical plane and also the horizontal plane. The degree to which the emission intensity moves from the vertical to horizontal plane is related to the mobility of the fluorescently labeled molecule. If the fluorescently labeled molecule is small, it will rotate or tumble faster, and the resulting emitted light will be depolarized relative to the excitation plane. If the fluorescently labeled molecule is very large, it will move very little during the excited state interval, and the emitted light will remain highly polarized with respect to the excitation plane. For example, for fluorophores attached to a small, rapidly rotating peptide the initially photoselected orientational distribution becomes randomized prior to emission, resulting in low fluorescence polarization. Conversely, binding of the peptide to a large, slowly rotating molecule (e.g., a high-molecular weight molecule) results in high fluorescence polarization. Fluorescence polarization measurements provide information on molecular orientation and mobility as well as processes that modulate these parameters, including proteolysis.

As used herein, the term "amino acid derivative" is an amino acid that has been modified. For example, amino acid derivatives include, but are not limited to, amino acid analogs. Likewise, amino acid derivatives include, but are not limited to, amino acids that have been modified to contain a functional group (e.g., a fluorophore).

As used herein, the term "authentic protein substrate" is a naturally occurring endogenous protein that is a substrate of a proteolytic ADAM33 polypeptide.

As used herein, the term "high throughput fluorescence device" is an instrument that measures fluorescence in a manner that permits high throughput automation of a screening process.

As used herein, the term "high performance liquid chromatography (HPLC) device" is an instrument that allows the separation of molecules under high pressure in a column filled with a matrix. Molecules are separated according to their physical properties such as their size, shape, charge, hydrophobicity, and affinity for other molecules. In general, the components to be separated are distributed between two phases: a stationary phase bed and a mobile phase which percolates through the stationary bed. A mixture of various components enters a chromatography process, and the different components are flushed through the system at different rates. These differential rates of migration as the mixture moves over adsorptive materials provide separation. Repeated sorption/desorption acts that take place during the movement of the sample over the stationary bed determine the rates. The smaller the affinity a molecule has for the stationary phase, the shorter the time spent in a column.

As used herein, the term "test compound" is a compound whose performance is measured in an assay. For example, the assay may measure whether the compound is a substrate of a proteolytic ADAM33 polypeptide. Alternatively, the assay may measure whether the compound is an inhibitor of the proteolytic activity of a proteolytic ADAM33 polypeptide. Test compounds include, but are not limited to, small molecules and peptides. Test compounds that inhibit the proteolytic activity of a proteolytic ADAM33 polypeptide may be useful for the treatment or prevention of a disease and/or condition involving the proteolytic action of ADAM33 (e.g., asthma).

As used herein, the term "inhibits" refers to the action of stopping or retarding an enzymatic reaction.

As used herein, the term "peptide" is a polymer of two or more amino acids joined together by peptide linkages. Similarly, the terms "polypeptide" and "protein" are used interchangeably with the term "peptide" although peptide (or oligopeptide) often denotes an amino acid sequence of fewer than 50 residues.

As used herein, the term "proteolytic ADAM33 polypeptide" is a polypeptide that is capable of catalyzing the proteolytic cleavage of a substrate (natural or artificial) of the native ADAM33 protease. A proteolytic ADAM33 polypeptide minimally comprises an active fragment of the ADAM33 catalytic domain that retains proteolytic activity. A proteolytic ADAM33 polypeptide includes, but is not limited to, a chimeric protein.

As used herein, the term "active fragment" of the catalytic domain of ADAM33" is a fragment of the catalytic domain of ADAM33 that retains about 10%, preferably about 20%, and more preferably about 25% of proteolytic activity of the wild-type ADAM33 protease (SEQ ID NO: 22). These activity measurements can be determined with the proteolytic assay provided herein. Preferably, the active fragment retains about 25%, more preferably about 50%, and even more preferably about 75% of the amino acid residues of the catalytic domain of ADAM33 having the amino acid sequence of SEQ ID NO: 22. More preferably, the amino acid sequence of the active fragment of the ADAM33 catalytic domain has about 95% identity to the corresponding amino acid residues of SEQ ID NO: 22.

As used herein, the term "chimeric" protein is meant to include "fusion proteins". "Chimeric" proteins of the present invention comprise at least a portion of a non-ADAM33 protein or peptide joined via a peptide bond to at least a portion of an ADAM33 catalytic domain. Chimeric proteins can have additional structural, regulatory, and/or catalytic properties. As used herein, a chimeric protein can contain multiple additions to at least a portion of an ADAM33 catalytic domain, e.g., it can comprise both a Ser-Gly-$His_6$Tag (SEQ ID NO: 23) and a secretion signaling signal, as exemplified below. In a particular embodiment the chimeric protein functions as a means of detecting and/or isolating the polypeptide or fragment thereof after a recombinant nucleic acid encoding the ADAM33 catalytic domain or fragment thereof is expressed. Non-ADAM33 amino acid sequences are preferably either amino- or carboxy-terminal to the ADAM33 sequence.

The present invention may be better understood by reference to the following non-limiting examples, which are provided as exemplary of the invention. These examples are presented in order to more fully illustrate the preferred embodiments of the invention and they should in no way be construed as limiting the scope of the invention.

Nucleic Acids Encoding ADAM33 Polypeptide

Obtaining and/or constructing a cDNA that encodes a polypeptide comprising an ADAM33 catalytic domain facilitates the production of large quantities of stable and active fragments of a proteolytic ADAM33 polypeptide required to perform standard enzyme assays. Such constructs can also contain heterologous nucleotide sequences. For example, an expression vector can be constructed containing nucleic acids encoding a polypeptide comprising the ADAM33 catalytic domain. The expression vector can be used in a suitable host cell (e.g., *Drosophila melanogaster* S2 cell line) to express the polypeptide comprising the ADAM33 catalytic domain. Alternatively, a viral vector can be constructed containing nucleic acids encoding a polypeptide comprising the ADAM33 catalytic domain which can be used in a suitable host cell to express the polypeptide comprising the ADAM33 catalytic domain.

Due to the degeneracy of nucleotide coding sequences, other DNA sequences which encode substantially the same amino acid sequence as a nucleic acid encoding a polypeptide comprising the ADAM33 catalytic domain or a modified ADAM33 catalytic domain may be used. These include, but are not limited to, allelic genes, homologous genes from other species, which are altered by the substitution of different codons that encode the same amino acid residue within the sequence, thus producing a silent change.

General methods for the cloning of cDNAs and expression of their corresponding recombinant proteins have been described [see Sambrook and Russell, *Molecular Cloning, A*

*Laboratory Manual*, 3rd edition, Cold Spring Harbor Laboratory Press, Cold Spring Harbor, N.Y. (2000)]. The particular methodology used herein is exemplified below.

The nucleotide sequence for open reading frame of wild-type ADAM33 with an SG linker, and a polyHis Tag (H6), SEQ ID NO: 23, is shown below (SEQ ID NO: 24). In particular, the pre domain can be the ADAM33 pre domain (SEQ ID NO: 25), or another secretion signal sequence that is derived from an eukaryotic organism or a virus. The BIP sequence, exemplified below, is derived from the *Drosophila* immunoglobulin binding chaperon protein, and is a preferred embodiment. Other possible pre domains can be employed including that from: PIPP (i.e. Pre-intermoult gene-1 protein precursor), HBM (i.e., Honeybee mellitin), H1C (i.e. Larval/pupal cuticle protein H1C precursor), LPM (i.e., Leucokinins precursor of mosquito *Aedes aegypti*), EGT (i.e., Baculovirus ecdysteroid UDP glucosyltransferase) and P67 (i.e., Baculovirus envelope glycoprotein P67).

In addition, polypeptides for use in the present invention include those that contain altered sequences such that functionally equivalent amino acid residues are substituted for residues within the ADAM33 catalytic domain sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs.

For example, the nonpolar amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, and

```
ADAM33:   MGWRPRRARGTPLLLLLLLLLLWPVPGAGVLQ   (SEQ ID NO: 25)

BIP:      MKLCILLAVVAFVGLSLG                 (SEQ ID NO: 26)

PIPP:     MKLTKLWLLFVCLGLFVTLVVS             (SEQ ID NO: 27)

HBM:      MKFLVNVNLVFMVVYISYIYA              (SEQ ID NO: 28)

H1C:      MYKFVVFAAALAYANA                   (SEQ ID NO: 29)

LPM:      MAMLLQVALPLLAAVSWG                 (SEQ ID NO: 30)

EGT:      MTILCWLALLSTLTAVNA                 (SEQ ID NO: 31)

P67:      MVSAIVLYVLLAAAAHSAFAAEHC           (SEQ ID NO: 32)
```

In addition, any technique for mutagenesis known in the art can be used to convert the native (wild-type) ADAM33 catalytic domain to a modified domain, including but not limited to, in vitro site-directed mutagenesis [Hutchinson et al., *J Biol Chem*, 253(18):6551–6560 (1978); Zoller and Smith, *DNA*, 3(6):479488 (1984); Oliphant et al., *Gene*, 44(2–3):177–183 (1986); Hutchinson et al., *Proc Natl Acad Sci USA*, 83(3):710–714 (1986)]. The use of TAB@ linkers (Pharmacia), etc. and PCR techniques also can be employed for site directed mutagenesis [see Higuchi, *Using PCR to Engineer DNA, in PCR Technology: Principles and Applications for DNA Amplification*, Erlich ed., Stockton Press, Chapter 6, pp. 61–70 (1989)].

Preferably mutagenesis (i.e., modification) of the ADAM33 catalytic domain is performed in a two step process [Wang, and Malcolm, *Bio Techniques*, 26(4):680–682 (1999)]. In the Example below, two extension reactions were performed in separate tubes in the first stage: (i) one containing the forward primer, and (ii) the other containing the reverse primer. After two cycles, the two reactions are mixed and the standard QuickChange mutagenesis procedure is carried out for an additional 18 cycles. Following amplification, the parental strand is digested with 1 Unit of Dpn1 for 1 hour and an aliquot is transformed into DH5-alpha cells [GeneWiz, New York, N.Y.]. Preferably all of the constructs are sequence confirmed.

ADAM33 Polypeptide

The wild-type ADAM33 protein fragment that was expressed in the *Drosophila* S2 cell line exemplified below, has the amino acid sequence set forth in SEQ ID NO: 33.

lysine. The negatively charged (acidic) amino acids include aspartic acid and glutamic acid.

Particularly preferred conserved amino acid exchanges are:

(a) Lys for Arg or vice versa such that a positive charge may be maintained;

(b) Glu for Asp or vice versa such that a negative charge may be maintained;

(c) Ser for Thr or vice versa such that a free —OH can be maintained;

(d) Gln for Asn or vice versa such that a polar amide can be maintained; and (e) Ile for Leu or for Val or vice versa as roughly equivalent hydrophobic amino acids.

The ADAM33 catalytic domain (or the modified ADAM33 catalytic domain) can be part of a chimeric protein. Such a chimeric protein can be a fusion protein which may used to isolate the chimeric protein through the use of an affinity column that is specific for the portion of a non-ADAM33 protein or peptide. In one such embodiment, the chimeric protein is expressed in an eukaryotic cell. Examples of such fusion proteins include: a glutathione-S-transferase (GST) fusion protein, a maltose-binding protein (MBP) fusion protein, a FLAG-tagged fusion protein, or as specifically exemplified below, a poly-histidine-tagged fusion protein. Specific linker sequences such as the Ser-Gly linker exemplified below can also be part of such a fusion protein.

Expression of a chimeric protein as a fusion protein can facilitate stable expression, and/or allow for purification based on the properties of the fusion partner. Thus purification of recombinant polypeptides can be simplified through the use of fusion proteins having affinity Tags. For example, GST binds glutathione conjugated to a solid support matrix, MBP binds to a maltose matrix, and poly-histidine chelates to a Ni-chelation support matrix, as specifically exemplified below [see Hochuli et al., *Bio/technology*, 6:1321–1325 (1998)]. The fusion protein can be eluted from the specific matrix with appropriate buffers, or by treating with a protease that is specific for a cleavage site that has been genetically engineered (e.g., in between the proteolytic ADAM33 polypeptide and its fusion partner). Alternatively, an ADAM33 catalytic domain can be combined with a detectable moiety, such as green fluorescent protein, that may be used for purification [Waldo et al., *Nat Biotechnol*, 17(7):691–695 (1999); U.S. Pat. No. 5,625,048 and WO 97/26333].

Alternatively or in addition, other column chromatography steps (e.g., gel filtration, ion exchange, affinity chromatography etc.) can be used to purify recombinant proteins. In many cases, such column chromatography steps employ high performance liquid chromatography or analogous methods in place of the more classical gravity-based procedures.

Specific details for the preferred purification procedure of recombinant and modified ADAM33 catalytic domains are provided in the Example below.

In addition, a method of expressing recombinant catalytic domains of zinc metalloproteins in eukaryotic host cells is provided in the Example below. Preferably, the recombinant Zinc metalloproteases have a "cysteine switch" [see Nagase and Woessner, *J Biol Chem*, 274(31):21491–21494 (1999)]. More preferably, the zinc metalloproteins are metalloproteases in the ADAM family. In this aspect of the invention, the catalytic domain. In a particular embodiment of this type, the expression of the recombinant metalloprotein is induced by 1–25 μM $Cd^{2+}$. In a preferred embodiment, 10 μM–1 mM $Zn^{2+}$ is included to optimize the amount of the catalytic domain obtained.

Preferably, the eukaryotic host cell is a *Drosophila* cell, and more preferably the *Drosophila* cell is from a *Drosophila melanogaster* Schneider 2 (S2) stable cell line. In a particular embodiment of this type, induction and optimization is achieved with 10 μM $Cd^{2+}$ and 200 μM $Zn^{2+}$.

In still another embodiment, polypeptides comprising the ADAM33 catalytic domain are chemically synthesized [see e.g., Synthetic Peptides: *A User's Guide*, W.H. Freeman & Co., New York, N.Y., pp. 382, Grant, ed. (1992)].

Cloning of Wild-Type and Modified ADAM33:

The cDNA sequence encoding the ADAM33 prodomain, catalytic domain, and a Ser-Gly-$His_6$ Tag (SEQ ID NO: 23) was amplified by PCR using a full length ADAM33 cDNA sequence with the following pair of PCR primers: 5' ATCTGATATC TCGAGTCAAT GATGGTGATG ATGATGTCCT GACGGGGCAT TGGAGAGGCA AGCGC 3' (SEQ ID NO: 34); and 5' TTAGATTCAT AGGGTACCGC TTCAAGGACA TATCCCTGGG CAG 3' (SEQ ID NO: 35). The PCR amplified cDNA was then digested with Kpn and Xho restriction enzymes and ligated into the *Drosophila* expression vector, pMT/Bip/V5-His-C (Invitrogen). The ligation mixture was then transfected into competent bacteria. The positive clones were identified by PCR screening and sequence confirmation.

The DNA open reading frame of the wild-type ADAM33 inserted in the cell line for expression was (SEQ ID NO: 24):

```
ATGAAGTTATGCATATTACTGGCCGTCGTGGCCTTTGTTGGCCTCTCGCTCGGGAGATCTCCATGGCCCGGGTAC
CGCTTCAAGGACATATCCCTGGGCAGCCAGTCACCCCGCACTGGGTCCTGGATGGACAACCCTGGCGCACCGTCAG
CCTGGAGGAGCCGGTCTCGAAGCCAGACATGGGGCTGGTGGCCCTGGAGGCTGAAGGCCAGGAGCTCCTGCTTGAG
CTGGAGAAGAACCACAGGCTGCTGGCCCCAGGATACATAGAAACCCACTACGGCCCAGATGGGCAGCCAGTGGTGC
TGGGCCCCCAACCACACGGATCATTGCCACTACCAAGGGCGAGTAAGGGGTTTCCCCGACTCCTGGGTAGTCCTCTG
CACCTGCTCTGGGATGAGTGGCCTGATCACCCTCAGCAGGAATGCCAGCTATTATCTGCGTCCCTGGCCACCCCGG
GGCTCCAAGGACTTCTCAACCCACGAGATCTTTCGGATGGAGCAGCTGCTCACCTGGAAAGGAACCTGTGGCCACA
GGGATCCTGGGAACAAAGCGGGCATGACCAGTCTTCCTGGTGGTCCCCAGAGCAGGGGCAGGCGAGAAGCGCGCAG
GACCCGGAAGTACCTGGAACTGTACATTGTGGCAGACCACACCCTGTTCTTGACTCGGCACCGAAACTTGAACCAC
ACCAAACAGCGTCTCCTGGAAGTCGCCAACTACGTGGACCAGCTTCTCAGGACTCTGGACATTCAGGTGGCGCTGA
CCGGCCTGGAGGTGTGGACCGAGCGGGACCGCAGCCGCGTCACGCAGGACGCCAACGCCACGCTCGGGCCTTCCT
GCAGTGGCGCCGGGGGCTGTGGGCGCAGCGGCCCCACGACTCCGCGCAGCTGCTCACGGGCCGCGCCTTCCAGGGC
GCCACAGTGGGCCTGGCGCCCGTCGAGGGCATGTGCCGCGCCGAGAGCTCGGGAGGCGTGAGCACGGACCACTCGG
AGCTCCCCATCGGCGCCGCAGCCACCATGGCCCATGAGATCGGCCACAGCCTCGGCCTCAGCCACGACCCCGACGG
CTGCTGCGTGGAGGCTGCGGCCGAGTCCGGAGGCTGCGTCATGGCTGCGGCCACCGGGCACCCGTTTCCGCGCGTG
TTCAGCGCCTGCAGCCGCCGCCAGCTGCGCGCCTTCTTCCGCAAGGGGGGCGGCGCTTGCCTCTCCAATGCCCCGT
CAGGACATCATCATCACCATCAT
```

$Cd^{2+}$ and/or $Zn^{2+}$ are employed to induce expression and/or to maximize the amount of the catalytic domain of the protein obtained. Preferably, a recombinant DNA construct is employed comprising a metallothionein promoter that is operatively linked to the nucleotide sequence that encodes The above nucleic acid sequence encodes (1) the "Pre" sequence (dashed line); (2) the linker sequence (wavy line); (3) the "prodomain" (the single underline); (4) the wild-type catalytic domain (unmarked); and (5) the SER-GLY-$HIS_6$ Tag (SEQ ID: 23) (double underlined).

Alternative "Pre", linker and "Tag" sequences can be readily substituted for the ones exemplified in SEQ ID NO: 24 above.

The amino acid sequence of the wild-type ADAM33 protein fragment expressed in the *Drosophila* S2 cell line was (SEQ ID NO: 33):

(PRE) MKLCILLAVVAFVGLSLG (LINKER) RSPWPGVP (PRODOMAIN) LQGHIPQPVTP
HWVLDGQPWRTVSLEEPVSKPDMGLVALEAEGQELLLELEKNHRLLAPGYIETHYGPDGQPV
VLAPNHTDHCHYQGRVRGFPDSWVVLCTCSGMSGLITLSRNASYYLRPWPPRGSKDFSTHEI
FRMEQLLTWKGTCGHRDPGNKAGMTSLPGGPQSRGRR (CAT) EARRTRKYLELYIVADHTLF
LTRHRNLNHTKQRLLEVANYVDQLLRTLDIQVALTGLEVWTERDRSRVTQDANATLWAFLQW
RRGLWAQRPHDSAQLLTGRAFQGATVGLAPVEGMCRAESSGGVSTDHSELPIGAAATMAHEI
GHSLGLSHDPDGCCVEAAAESGGCVMAAATGHPFPRVFSACSRRQLRAFFRKGGGACLSNAP
SGHHHHHH

The amino acid sequence of (1) the "Pre" sequence (dashed line); (2) the linker sequence (wavy line); (3) the "prodomain" (the single underline); (4) the wild-type catalytic domain (unmarked); and (5) the SER-GLY-$HIS_6$ Tag (double underlined) (SEQ ID NO: 23).

The amino acid sequence of the wild-type ADAM33 catalytic domain is:

EARRTRKYLELYIVADHTLFLTRHRNLNHTKQRLLEVANYVDQLLRTLDIQVALTGLEVWTE (SEQ ID NO: 22)
RDRSRVTQDANATLWAFLQWRRGLWAQRPHDSAQLLTGRAFQGATVGLAPVEGMCRAESSGG
VSTDHSELPIGAAATMAHEIGHSLGLSHDPDGCCVEAAAESGGCVMAAATGHPFPRVFSACS
RRQLRAFFRKGGGACLSNAP

Establishment of *Drosophila melanogaster* Schneider 2 (S2) Stable Cell Lines:

Stable cell lines were produced by utilizing the *Drosophila* Expression System (Invitrogen, Carlsbad, Calif., USA). *Drosophila* S2 cells were transfected with ADAM33 recombinant DNA and the selection vector pCoHygro. Hygromycin resistant cell lines were selected for 6–8 weeks, and were stored in liquid nitrogen for an unlimited time.

Expression and Purification of Wild-Type and Mutant ADAM33:

Stable cell lines containing the recombinant DNA were grown to $10–20\times10^6$ cells/ml in complete DES® Expression Medium (Invitrogen) supplemented with 0.3 mg/ml hygromycin, and 0.1% Pluronic F-68. The cells were collected using centrifugation at 1000 g for 15 minutes. The cell pellet was immediately suspended in *Drosophila* Serum-Free Medium supplemented with 1% DMSO and 0.1% Pluronic F-68 (Invitrogen, Carlsbad, Calif., USA) at a cell density of $2–4\times10^6$ cells/ml, and allowed to grow for 16–24 hours. Expression of ADAM33 was induced using 10 μM $CdCl_2$ in the presence of 200 μM $ZnCl_2$. The secreted ADAM33 was isolated from the conditioned media after clarification by centrifugation. 1M HEPES pH 7.3 (Fischer # BP299-1) was added to the supernatant so that the final concentration of HEPES was 25 mM. An equal volume of buffer A (25 mM HEPES, pH 7.0, 10% glycerol) was added to reduce the conductivity, and the sample was applied to a SP-SEPHAROSE FF cation exchange column (Amersham Pharmacia, Piscataway, N.J.).

The SP-SEPHAROSE FF column was washed with 10 column volumes (CV) of buffer A with 100 mM NaCl, and fractions of 1 CV were collected during elution with a salt gradient from 100–500 mM NaCl (Buffer B: 25 mM HEPES, pH7.9, 10% glycerol, 500 mM NaCl). The fractions containing the ADAM33 catalytic domain were pooled, 5 mM imidazole was added, and the sample was applied to a Ni-NTA column equilibrated in buffer C (25 mM HEPES, pH7.9, 10% glycerol, 500 mM NaCl, 5 mM Imidazole).

The Ni-NTA column was washed with 15–20 CV of buffer C until a stable baseline was achieved, and the protein was eluted with 250 mM imidazole in buffer C. The eluted protein was concentrated to 5–15 mg/ml, and then applied to a SUPERDEX-75 gel filtration column equilibrated with buffer GF (25 mM HEPES, pH 7.5, 150 mM NaCl, 10% glycerol, 50 mM imidazole). Fractions corresponding to the monomer of ADAM33 were pooled, and diluted to 0.3 mg/ml, flash-frozen in liquid nitrogen, and stored at −80° C. The presence of imidazole facilitated the separation of the prodomain from the catalytic domain, but also stabilizes the purified protein. As required, the frozen protein was thawed on ice and concentrated to 10 mg/ml using Ultrafree®-15 Centrifugation Filter Device (Millipore, Bedford, Mass.). 5 mM $CaCl_2$ is preferably included throughout the purification process. It is also preferred that 5 mM $CaCl_2$ is retained in the storage buffer.

Synthesis of ADAM33 Peptide Substrates

Peptide substrates of a proteolytic ADAM33 polypeptide can be synthesized by any of the well known peptide synthesis methods, such as by exclusive solid phase synthesis, partial solid phase methods, fragment condensation or classical solution synthesis. The peptides are preferably prepared by solid phase peptide synthesis as described by Merrifield [Merrifield, *J Am Chem Soc*, 85(14):2149–2154 (1963)]. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups (e.g., benzyloxycarbonyl (Cbz), substituted benzyloxycarbonyl and 9-fluorenylmethyloxy-carbonyl (Fmoc)), aliphatic urethane protecting groups (e.g., t-butyloxycarbonyl (tBoc), isopropyloxycarbonyl, cyclohexyloxycarbonyl) and alkyl type protecting groups (e.g., benzyl, triphenylmethyl). The preferred protecting groups are tBoc and Fmoc, thus the peptides are said to be synthesized by tBoc and Fmoc chemistry, respectively. The more preferred protecting group for the present invention is Fmoc.

The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In tBoc chemistry, the preferred side-chain protecting groups are tosyl for Arg, cyclohexyl for Asp, 4-methylbenzyl (and acetamidomethyl) for Cys, benzyl for Glu, Ser and Thr, benzyloxymethyl (and dinitrophenyl) for His, 2-Cl-benzyloxycarbonyl for Lys, formyl for Trp and 2-bromobenzyl for Tyr. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for Arg, trityl for Asn, Cys, Gln and His, tert-butyl for Asp, Glu, Ser, Thr and Tyr, tBoc for Lys and Trp.

For the synthesis of phosphopeptides, either direct or post-assembly incorporation of the phosphate group is used. In the direct incorporation strategy, the phosphate group on Ser, Thr or Tyr may be protected by methyl, benzyl or tert-butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl group of Ser, Thr or Tyr was derivatized on solid phase with di-tert-butyl-, dibenzyl- or dimethyl-N,N'-diisopropylphosphoramidite and then oxidized by tert-butylhydroperoxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) is used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available and their preparations have been described. [See Stewart et al., *Solid Phase Peptide Synthesis*, 2$^{nd}$ Edition, Pierce Chemical Co., Rockford, Ill. (1984); and Bayer & Rapp, *Chem Pept Prot*, 3:3–8 (1986); and Atherton, et al., *Solid Phase Peptide Synthesis: A Practical Approach*, IRL Press, Oxford (1989)].

The C-terminal amino acid, protected at the side-chain if necessary and at the alpha-amino group, is attached to a hydroxylmethyl resin using various activating agents including dicyclohexylcarbodiimide (DCC), N,N'-diisopropylcarbodiimide DIPCDI) and carbonyldiimidazole (CDI). It can be attached to chloromethyl or chlorotrityl resin directly in its cesium tetramethylammonium salt form or in the presence of triethylamine (TEA) or diisopropylethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, ,Fmoc). The extent of Fmoc removal can be monitored at 300–320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethylamino)-phosphonium hexafluorophosphate (BOP) and its pyrrolidine analog (PyBOP), bromo-tris-pyrrolidino-phosphonium hexafluorophosphate (PyBroP), O-(benzotriazol-1-yl)-1,1,3,3-tetramethyluronium hexafluorophosphate (HBTU) and its tetrafluoroborate analog (TBTU) or its pyrrolidine analog (HBPyU), O-(7-azabenzotriazol-1-yl)-1,1,3,3-tetramethyluronium hexafluorophosphate (HATU) and its tetrafluoroborate analog (TATU) or pyrrolidine analog (HAPyU). The most common catalytic additives used in coupling reactions include 4-dimethylaminopyridine (DMAP), 3-hydroxy-3,4-dihydro4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction can be monitored at each stage, e.g., by the ninhydrin reaction as described by Kaiser et al. [Kaiser et al., *Anal Biochem*, 34(2):595–598 (1970)]. In cases where incomplete coupling is found, the coupling reaction is extended and repeated and may have chaotropic salts added. The coupling reactions can be performed automatically with commercially available instruments such as ABI model 430A, 431A and 433A peptide synthesizers.

After the entire assembly of the desired peptide, the peptide-resin is cleaved with a reagent with proper scavengers. The Fmoc peptides are usually cleaved and deprotected by TFA with scavengers (e.g., $H_2O$, ethanedithiol, phenol and thioanisole). The tBoc peptides are usually cleaved and deprotected with liquid HF for 1–2 hours at −5° to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of Trp and dinitrophenyl group of His need to be removed, respectively, by piperidine and thiophenol in DMF prior to the HF cleavage. The acetamidomethyl group of Cys can be removed by mercury (II) acetate and alternatively by iodine, thallium (III) trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTF).

Recombinant DNA methodology can also be used to prepare the polypeptide substrates. The known genetic code, tailored if desired with known preferred codons for more efficient expression in a given host organism, can be used to synthesize oligonucleotides encoding the desired amino acid sequences. The phosphoramidite solid support method of Matteucci et al. [Matteucci et al., *J Am Chem Soc*, 103(11): 3185–3191 (1981)] or other known methods can be used for such syntheses. The resulting oligonucleotides can be inserted into an appropriate vector and expressed in a compatible host organism.

The peptides of the invention can be purified using HPLC, gel filtration, ion exchange and partition chromatography, countercurrent distribution or other well known methods.

Relative Activity of ADAM33 Substrates

In searching for substrates of a proteolytic ADAM33 polypeptide, a 28-mer peptide (APP28) (SEQ ID NO: 36) derived from amyloid precursor protein was identified as a weakly cleavable peptide. Truncation of APP28 led to identification of a 10-mer peptide substrate of a proteolytic ADAM33 polypeptide (SEQ ID NO: 8). Alanine-scanning of the 10-mer peptide substrate for determining the structure activity relationship led to the identification of another ADAM33 substrate, Ac-Tyr-Glu-Val-Ala-His-Gln-Lys-Leu-Val-Phe-NH2 (SEQ ID NO: 13), which is efficiently cleaved (kcat/Km=10,000 M-1s-1) at a rate seventeen times greater than the 10-mer truncated form of APP28 (SEQ ID NO: 8). See Table 1 for the relative proteolytic activity of several peptide substrates of a proteolytic ADAM33 polypeptide.

substrates of a proteolytic ADAM33 polypeptide permits high throughput assay development for identification of compounds that inhibit the proteolytic activity of a proteolytic ADAM33 polypeptide.

Assays for Measuring Proteolytic Activity of ADAM33

Proteolytic activity of a proteolytic ADAM33 polypeptide can be determined in any of a number of relatively standard protease assay formats. This following is a non-limiting list of assays which are provided as exemplary assays that may be used to determine proteolytic activity. Such assays may be used in methods to identify additional substrates of a proteolytic ADAM33 polypeptide as well as to identify inhibitors of a proteolytic ADAM33 polypeptide.

In addition, such assays may be used with high throughput fluorescent devices or high performance liquid chromatography for screening at a high throughput. For example, using the assays described below, and a dedicated BIAcore™ instrument, at least 1000 samples per week can be screened for either their proteolytic activity or their inhibitory effects toward the proteolytic activity, in a 96-well plate format.

The proteolytic activity assay consists of a substrate, preferably at a micromolar to submicromolar concentration, and a proteolytic ADAM33 polypeptide, preferably at a submicromolar concentration, in a benign buffered solution at pH 7–9, more preferably around pH 7.5–8.0. This assay may be set-up to monitor proteolytic activity of a proteolytic ADAM33 polypeptide continuously over a time span of minutes to hours in a 96-well or 384-well format. Alternatively, this assay may be set up to allow an elapse of time span of minutes to hours before the proteolytic activity is quenched and analyzed following acidification to under pH 4 or addition of an excess amount of zinc chelators (e.g., EDTA).

For example, an ADAM33 substrate derived from amyloid percursor protein to assay the proteolytic activity of a proteolytic ADAM33 polypeptide. The cleavage site in the above-mentioned substrate is indicated by a hyphen (i.e., the

TABLE 1

Structure Activity Relationship of Peptide Substrates

| SEQ ID NO: | Code | Peptide Substrate Sequence | Relative Activity |
|---|---|---|---|
| 11 | P7P7' | SGYEVAH*QKLAFFA-OH | 1.2 |
| 9 | P7P4' | SGYEVAH*QKLA-OH | 0.5 |
| 13 | P5P5' | Ac-YEVAH*QKLVF-$NH_2$ | 1.0 |
| 7 | P5P5' | YEVAH*QKLAF-OH | 1.1 |
| 12 | P5P4' | YEVAH*QKLA-OH | 0.9 |
| 37 | P4P4' | EVAH*QKLA-OH | 0.1 |
| 38 | P3P3' | Ac-VAH*QKL-$NH_2$ | 0.0 |

Peptide substrates of ADAM33 were designed for high throughput assay based on fluorescence polarization or fluorescence resonance energy transfer (including quenching). Full positional scanning of peptide substrates using structure activity relationship studies revealed the positional preference (substrate specificity profile) for ADAM33. This information can be useful in the identification of additional peptide substrates of a proteolytic ADAM33 polypeptide as well as the identification of an authentic protein substrate of wild-type ADAM33 protein. Furthermore, the availability of cleavage site is the scissile bond being between the second histidine and the adjacent glutamine). One particular set of assay conditions contains 25 nM of the proteolytic ADAM33 polypeptide and 25 μM substrate. The reaction is initiated in 25 mM Hepes, pH 8.0, 2M NaCl by mixing the enzyme with the substrate. The rate of reaction is measured over a defined time period (e.g., for 1 hour at room temperature) and then stopped. Product formation can be quantified at 214 nm by HPLC using a reverse phase column to separate the substrate from the products. An HPLC assay for proteolytic activity is described by Lammich et al. [Lammich et al., *Proc Natl Acad Sci USA*, 96(7):3922–3927 (1999)].

Fluorescence Polarization Assay:

A fluorescence polarization assay may be used to determine the cleavage of a peptide substrate or potential peptide substrate by a proteolytic ADAM33 polypeptide. The assay would be conducted as described above with a peptide substrate or potential peptide substrate that contains a protein marker. A high molecular weight molecule (preferably >20 KD) that is capable of binding to the protein marker on the peptide is added before the polarization value is read. For example, if the protein marker on the peptide is biotin, then avidin (which binds to biotin) may be added before the polarization value is read. [Fluorescence polarization is described, for example, by Turek et al., *Anal Biochem*, 299(1):45–53 (2001); and Owicki, *J Biomol Screen*, 5(5): 297–306 (2000)].

Surface Plasmon Resonance:

The proteolytic activity of a proteolytic ADAM33 polypeptide can be determined by following the extent of cleavage of a substrate of the proteolytic ADAM33 polypeptide using surface plasmon resonance (SPR) spectroscopy [U.S. Pat. No. 5,981,167].

In a particular embodiment the substrate is Biotin-YEVHH-QKLVF-phosphotyrosine (SEQ ID NO: 39). In an alternative embodiment, the substrate is Biotin-WEVAHQKLAK-phosphotyrosine-NH2 (SEQ ID NO: 40). The substrate and a proteolytic ADAM33 polypeptide are placed in a reaction mixture under conditions that allow the protease to cleave the substrate. The reaction is stopped at a set time and then brought into contact with an anti-phosphotyrosine antibody bound to a sensor chip under conditions that allow the antibody to bind the substrate. The amount of cleavage is determined by comparing the mass of the intact substrate with the mass of the cleaved substrate as detected by surface plasmon resonance technology.

The SPR-based assay for a proteolytic ADAM33 polypeptide described above can also be used to determine if a test compound inhibits the proteolytic activity of the proteolytic ADAM33 polypeptide. In one such assay, a test compound is placed in the reaction mixture with the proteolytic ADAM33 polypeptide and the Biotin-YEVHH-QKLVF-phosphotyrosine substrate (SEQ ID NO: 39). The reaction is stopped at a set time and then brought into contact with an anti-phosphotyrosine antibody bound to a sensor chip under conditions that allow the antibody to bind the substrate. The amount of cleavage is determined by comparing the mass of the intact substrate with the mass of the cleaved substrate as detected by surface plasmon resonance technology. The test compound is identified as an inhibitor of the proteolytic activity of the proteolytic ADAM33 polypeptide when the amount of substrate cleaved in the reaction mixture is less in the presence of test compound as compared to the amount of substrate cleaved in the absence of test compound.

Fluorescence Resonance Energy Transfer (FRET) Assay:

A FRET assay may also be used to determine the cleavage of a compound by a proteolytic ADAM33 polypeptide. At room temperature, in a total reaction volume of 100 μL per well in a 96 well plate, add 50 μL of 2× Assay Buffer (40 mM HEPES, pH 7.5, 1.0 M NaCl; 1× Assay Buffer being 20 mM HEPES, pH 7.5, 0.5 M NaCl), followed by 25 μL of 100 μM substrate, e.g., SEQ ID NO: 14 (K(Dabcyl)YEVAHQKLAE (Edans)K-OH), and lastly 25 μL of 40 nM a proteolytic ADAM33 polypeptide in Enzyme Dilution Buffer 40 mM HEPES, pH 7.5. The reaction starts after the enzyme is added and is assayed at room temperature for 15–20 minutes by reading the relative fluorescence unit.

High Throughput Screening Using FRET Assay:

For High throughput screening, the FRET assay is performed similarly to that stated above, but with Assay Buffer that is also composed of 0.2 mg/ml BSA (1× Assay Buffer being 20 mM HEPES, pH 7.5, 0.5 M NaCl, 0.2 mg/ml BSA). In addition, the substrate used has a fluorescent donor and an acceptor at either end of the peptide, e.g., SEQ ID NO: 18 ((Cy5Q)WEVAH*QKLAC(Cy3B)K). Lastly, the reaction is incubated at room temperature for 3 hours and then stopped by adding 10 μL EDTA (11 mM). To measure the proteolytic activity of the proteolytic ADAM33 polypeptide on the substrate, the endpoint (relative fluorescence unit) is read using the appropriate excitation and emission wavelengths (e.g., for Cy5Q and Cy3B, 540 nm and 580 nm, respectively). For example, use of the acceptor Dabcyl in conjunction with the fluorescent donor Edans is described in a FRET assay by Matayoshi et al. [Matayoshi et al., *Science*, 247 (4945):954–958 (1990)].

Assay for Identifying Substrates of ADAM33

Test compounds can be assayed (as described above) to determine if they are substrates of a proteolytic ADAM33 polypeptide. Briefly, by contacting a proteolytic ADAM33 polypeptide with a test compound and measuring cleavage of the test compound, one can determine whether the test compound is a substrate of the proteolytic ADAM33 polypeptide. Specifically, cleavage of the test compound indicates that the test compound is a substrate of the proteolytic ADAM33 polypeptide. Such an assay may also be used to identify authentic protein substrates of a proteolytic ADAM33 polypeptide.

Assay for Identifying Inhibitors of ADAM33

Test compounds can be assayed (as described above) to determine if they inhibit proteolytic activity of a proteolytic ADAM33 polypeptide. Briefly, by contacting a proteolytic ADAM33 polypeptide with a substrate of a proteolytic ADAM33 polypeptide and measuring cleavage of the substrate in the presence and absence of a test compound, one can determine whether the test compound is an inhibitor of the proteolytic activity of the proteolytic ADAM33 polypeptide. Specifically, a decrease in cleavage of the substrate in the presence of the test compound indicates that the test compound inhibits the proteolytic activity of the proteolytic ADAM33 polypeptide.

Potential Inhibitors of the Proteolytic Activity of ADAM33

Test compounds that are potential inhibitors of the proteolytic activity of ADAM33 can be selected from a variety of sources. For example, compounds known to bind a proteolytic ADAM33 polypeptide, or a compound that inhibits the closely related TACE protease [e.g., Letavic et al., *Biorg Med Chem Lett*, 12(10):1387–1390 (2002), Duan et al., *J Med Chem*, 45(23):4954–4957 (2002)], or alternatively, a compound that binds metalloproteases as disclosed as by Zask et al. [Zask et al., *Curr Pharm Des*, 2(6):624–661 (1996)], can be assayed for inhibitory activity and systematically modified until one or more promising potential analogs are identified. Such analysis has been shown to be effective in the development of HIV protease inhibitors [Lam et al., *Science*, 263(5145):380–384 (1994); Wlodawer et al., *Ann Rev Biochem*, 62:543–585 (1993); Appelt, *Perspect Drug Discov*, 1(1):23–48 (1993); Erickson, *Perspect Drug Discov*, 1(1):109–128 (1993)]. Alternatively, a potential inhibitor initially can be obtained by screening a random peptide library or a chemical library. In the former case, a random peptide library can be produced by recombinant bacteriophage [for example, as described by Scott and Smith, *Science*, 249(4967):386–390 (1990); Cwirla et al., *Proc Natl Acad Sci USA*, 87(16):6378–6382 (1990); and Devlin et al., *Science*, 249(4967):404–406 (1990)].

If a potential inhibitor is a small organic compound, it either can be selected from a library of chemicals, as are commercially available from most large chemical companies, including Merck, GlaxoSmithKline, Bristol Meyers Squib, Monsanto/Searle, Eli Lilly, Novartis, Aventis and Pfizer. Alternatively, the small organic compound may be synthesized de novo. The de novo synthesis of one or even a relatively small group of specific compounds is reasonable in the art of drug design. Once obtained, the potential inhibitor can be further tested in a proteolytic assay (described above) and/or in a binding assay (described below) with a proteolytic ADAM33 polypeptide.

For example, a binding assay can be performed following the attachment of the proteolytic ADAM33 polypeptide to a solid support. Methods for placing the proteolytic ADAM33 polypeptide on the solid support are well known in the art and include such things as linking biotin to the proteolytic ADAM33 polypeptide and linking avidin to the solid support. The solid support can be washed to remove unbound protein. A solution of a labeled potential inhibitor can be contacted with the solid support. The solid support is washed again to remove the potential inhibitor not bound to the support. The amount of labeled potential inhibitor remaining with the solid support, and thereby bound to the proteolytic ADAM33 polypeptide can be determined. Alternatively, or in addition, the dissociation constant between the labeled potential inhibitor and the proteolytic ADAM33 polypeptide, for example, can be determined. Suitable labels for either the proteolytic ADAM33 polypeptide or the potential inhibitor include, radioactive labels (e.g., $^{14}C$, $^{1}H$,) and fluorescent labels such as fluorescein isothiocyanate (FITC).

In another embodiment, a Biacore™ machine can be used to determine the binding constant of the proteolytic ADAM33 polypeptide with a potential inhibitor [O'Shannessy et al., *Anal Biochem*, 212(2):457468 (1993); Schuster et al., *Nature*, 365(6444):343–347 (1993)].

Inhibitor of a Proteolytic ADAM33 Polypeptide

Using the FRET assay described above, the TACE inhibitor marimastat has been identified as an inhibitor of the proteolytic activity of a proteolytic ADAM33 polypeptide.

Other

Additional peptide substrates and inhibitors of ADAM33 protease or active fragment thereof, as well as related assays for identifying substrates and/or inhibitors of ADAM33 protease or active fragment thereof are disclosed in Examples 2 and 3 of United States patent application entitled "Catalytic Domain of ADAM33 and Methods of Use Thereof" in the name of inventors Wenyan Wang et al. filed concurrently herewith. Likewise, the association of human ADAM33 prodomain (PRO) and catalytic domain (CAT) and assays for determining the same are disclosed in Example 4 of the aforementioned United States patent application.

The present invention is not to be limited in scope by the specific embodiments describe herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. An isolated peptide comprising the amino acid sequence EVAHQKLA (SEQ ID NO: 37) or Ac-YEVAHQKLVF-$NH_2$ (SEQ ID NO: 13).

2. The peptide of claim 1 comprising the amino acid sequence YEVAHQKLA (SEQ ID NO: 12).

3. The peptide of claim 2 comprising the amino acid sequence YEVAHQKLAF (SEQ ID NO: 7).

4. The peptide of claim 1 comprising the amino acid sequence SGYEVAHQKLA (SEQ ID NO: 9).

5. The peptide of claim 4 comprising the amino acid sequence SGYEVAHQKLAFFA (SEQ ID NO: 11).

6. An isolated peptide comprising one conservative amino acid substitution in an amino acid sequence selected from the group consisting of EVAHQKLA (SEQ ID NO: 37) and Ac-YEVAHQKLVF-NH2 (SEQ ID NO: 13).

7. The peptide of claim 1 fused to a detectable moiety.

8. The peptide of claim 7 wherein the detectable moiety is selected from the group consisting of:

a) a fluorescent donor;

b) an acceptor;

c) a fluorophore; and d) a protein marker.

9. The peptide of claim 8 wherein:

a) the fluorescent donor is selected from the group consisting of Edans, Mca, Cy3B, and Alexa Fluor 546;

b) the acceptor is selected from the group consisting of Alexa Fluor 647, Cy5, Dabcyl, Dnp, and Cy5Q;

c) the fluorophore is selected from the group consisting of fluorescein, rhodamine, Texas red, and BODIPY derivatives; or d) the protein marker is selected from the group consisting of biotin, digoxin, and phosphotyrosine.

10. A method for identifying whether a test compound inhibits proteolytic activity of a proteolytic ADAM33 polypeptide comprising:

a) contacting the proteolytic ADAM33 polypeptide with a substrate of the proteolytic ADAM33 polypeptide;

b) measuring cleavage of the substrate;

c) adding the test compound;

d) measuring cleavage of the substrate in the presence of the test compound;

wherein a decrease in cleavage of the substrate in the presence of the test compound indicates that the test compound inhibits the proteolytic activity of the proteolytic ADAM33 polypeptide.

11. The method of claim 10 wherein the substrate comprises an amino acid sequence selected from the group consisting of:

SGYEVAHQKLAFFA-OH (SEQ ID NO: 11);
SGYEVAHQKLA-OH (SEQ ID NO: 9);
Ac-YEVAHQKLVF-NH2 (SEQ ID NO: 13);
YEVAHQKLAF-OH (SEQ ID NO: 7);
YEVAHQKLA-OH (SEQ ID NO: 12); and
EVAHQKLA-OH (SEQ ID NO: 37).

12. The method of claim 10 wherein the measuring uses a high throughput fluorescence device or a high performance liquid chromatography device.

13. An isolated peptide consisting of an amino acid sequence selected from the group consisting of: SGYEVAHQKLAFFA-OH (SEQ ID NO: 11);

SGYEVAHQKLA-OH (SEQ ID NO: 9);
Ac-YEVAHQKLVF-NH2 (SEQ ID NO: 13);
YEVAHQKLAF-OH (SEQ ID NO: 7);
YEVAHQKLA-OH (SEQ ID NO: 12); and
EVAHQKLA-OH (SEQ ID NO: 37).

* * * * *

SEQUENCE LISTING

<160> NUMBER OF SEQ ID NOS: 40

<210> SEQ ID NO 1
<211> LENGTH: 9
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa = Trp, Tyr, Phe, Ile, Leu, Met, Val, or an
analog thereof
<220> FEATURE:
<221> NAME/KEY: MISC_FEATURE
<222> LOCATION: (9)..(9)
<223> OTHER INFORMATION: Xaa = Trp, Ala, Ile, Leu, Met, Val, Phe, Tyr,
Arg, His, Lys, or an analog thereof

<400> SEQUENCE: 1

Xaa Glu Val Ala His Gln Lys Leu Xaa
1 5

<210> SEQ ID NO 2
<211> LENGTH: 9
<212> TYPE: PRT
<213> ORGANISM: Artificial
<220> FEATURE:
<223> OTHER INFORMATION: synthetic peptide

```
<220> FEATURE:
<221> NAME/KEY: MISC_FEATURE
<222> LOCATION: (1)..(1)
<223> OTHER INFORMATION: Xaa = Trp or Tyr
<220> FEATURE:
<221> NAME/KEY: MISC_FEATURE
<222> LOCATION: (9)..(9)
<223> OTHER INFORMATION: Xaa = Ala or Val

<400> SEQUENCE: 2

Xaa Glu Val Ala His Gln Lys Leu Xaa
1               5


<210> SEQ ID NO 3
<211> LENGTH: 10
<212> TYPE: PRT
<213> ORGANISM: Artificial
<220> FEATURE:
<223> OTHER INFORMATION: synthetic peptide

<400> SEQUENCE: 3

Tyr Glu Val Ala His Gln Lys Leu Val Phe
1               5                   10


<210> SEQ ID NO 4
<211> LENGTH: 11
<212> TYPE: PRT
<213> ORGANISM: Artificial
<220> FEATURE:
<223> OTHER INFORMATION: synthetic peptide

<400> SEQUENCE: 4

Tyr Glu Val Ala His Gln Lys Leu Ala Glu Lys
1               5                   10


<210> SEQ ID NO 5
<211> LENGTH: 11
<212> TYPE: PRT
<213> ORGANISM: Artificial
<220> FEATURE:
<223> OTHER INFORMATION: synthetic peptide

<400> SEQUENCE: 5

Trp Glu Val Ala His Gln Lys Leu Ala Cys Lys
1               5                   10


<210> SEQ ID NO 6
<211> LENGTH: 12
<212> TYPE: PRT
<213> ORGANISM: Artificial
<220> FEATURE:
<223> OTHER INFORMATION: synthetic peptide

<400> SEQUENCE: 6

Lys Tyr Glu Val Ala His Gln Lys Leu Ala Glu Lys
1               5                   10


<210> SEQ ID NO 7
<211> LENGTH: 10
<212> TYPE: PRT
<213> ORGANISM: Artificial
<220> FEATURE:
<223> OTHER INFORMATION: synthetic peptide

<400> SEQUENCE: 7

Tyr Glu Val Ala His Gln Lys Leu Ala Phe
1               5                   10
```

```
<210> SEQ ID NO 8
<211> LENGTH: 10
<212> TYPE: PRT
<213> ORGANISM: Artificial
<220> FEATURE:
<223> OTHER INFORMATION: synthetic peptide

<400> SEQUENCE: 8

Tyr Glu Val His His Gln Lys Leu Val Phe
1               5                   10


<210> SEQ ID NO 9
<211> LENGTH: 11
<212> TYPE: PRT
<213> ORGANISM: Artificial
<220> FEATURE:
<223> OTHER INFORMATION: synthetic peptide

<400> SEQUENCE: 9

Ser Gly Tyr Glu Val Ala His Gln Lys Leu Ala
1               5                   10


<210> SEQ ID NO 10
<211> LENGTH: 12
<212> TYPE: PRT
<213> ORGANISM: Artificial
<220> FEATURE:
<223> OTHER INFORMATION: synthetic peptide

<400> SEQUENCE: 10

Lys Tyr Glu Val Ala His Gln Lys Leu Ala Lys Lys
1               5                   10


<210> SEQ ID NO 11
<211> LENGTH: 14
<212> TYPE: PRT
<213> ORGANISM: Artificial
<220> FEATURE:
<223> OTHER INFORMATION: synthetic peptide

<400> SEQUENCE: 11

Ser Gly Tyr Glu Val Ala His Gln Lys Leu Ala Phe Phe Ala
1               5                   10


<210> SEQ ID NO 12
<211> LENGTH: 9
<212> TYPE: PRT
<213> ORGANISM: Artificial
<220> FEATURE:
<223> OTHER INFORMATION: synthetic peptide

<400> SEQUENCE: 12

Tyr Glu Val Ala His Gln Lys Leu Ala
1               5


<210> SEQ ID NO 13
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION
```

<400> SEQUENCE: 13

Tyr Glu Val Ala His Gln Lys Leu Val Phe
1 5 10

<210> SEQ ID NO 14
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Dabcyl detectable moiety attached to side chain
<220> FEATURE:
<221> NAME/KEY: MISC_FEATURE
<222> LOCATION: (11)..(11)
<223> OTHER INFORMATION: Edans detectable moiety attached to side chain

<400> SEQUENCE: 14

Lys Tyr Glu Val Ala His Gln Lys Leu Ala Glu Lys
1 5 10

<210> SEQ ID NO 15
<211> LENGTH: 12
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Mca detectable moiety attached to side chain
<220> FEATURE:
<221> NAME/KEY: MISC_FEATURE
<222> LOCATION: (11)..(11)
<223> OTHER INFORMATION: Dnp detectable moiety attached to side chain

<400> SEQUENCE: 15

Lys Tyr Glu Val Ala His Gln Lys Leu Ala Lys Lys
1 5 10

<210> SEQ ID NO 16
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Dabcyl detectable moiety attached to N-terminus
<220> FEATURE:
<221> NAME/KEY: MISC_FEATURE
<222> LOCATION: (10)..(10)
<223> OTHER INFORMATION: Edans detectable moiety attached to side chain

<400> SEQUENCE: 16

Tyr Glu Val Ala His Gln Lys Leu Ala Glu Lys
1 5 10

<210> SEQ ID NO 17
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Cy3B detectable moiety attached to N-terminus -continued
<220> FEATURE:
<221> NAME/KEY: MISC_FEATURE
<222> LOCATION: (10)..(10)
<223> OTHER INFORMATION: Cy5Q detectable moiety attached to side chain

<400> SEQUENCE: 17

Trp Glu Val Ala His Gln Lys Leu Ala Cys Lys
1 5 10

<210> SEQ ID NO 18
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Cy5Q detectable moiety attached to N-terminus
<220> FEATURE:
<221> NAME/KEY: MISC_FEATURE
<222> LOCATION: (10)..(10)
<223> OTHER INFORMATION: Cy3B detectable moiety attached to side chain

<400> SEQUENCE: 18

Trp Glu Val Ala His Gln Lys Leu Ala Cys Lys
1 5 10

<210> SEQ ID NO 19
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Biotin detectable moiety attached to N-terminus
<220> FEATURE:
<221> NAME/KEY: MISC_FEATURE
<222> LOCATION: (10)..(10)
<223> OTHER INFORMATION: Alexa Fluor 568 detectable moiety attached to side chain

<400> SEQUENCE: 19

Trp Glu Val Ala His Gln Lys Leu Ala Cys Lys
1 5 10

<210> SEQ ID NO 20
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Biotin detectable moiety attached to N-terminus
<220> FEATURE:
<221> NAME/KEY: MISC_FEATURE
<222> LOCATION: (10)..(10)
<223> OTHER INFORMATION: Alex Fluor 594 detectable moiety attached to side chain

<400> SEQUENCE: 20

Trp Glu Val Ala His Gln Lys Leu Ala Cys Lys
1 5 10

-continued

```
<210> SEQ ID NO 21
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Biotin detectable moiety attached to N-terminus
<220> FEATURE:
<221> NAME/KEY: MISC_FEATURE
<222> LOCATION: (10)..(10)
<223> OTHER INFORMATION: Alexa Fluor 647 or Cy5 detectable moiety
      attached to side chain

<400> SEQUENCE: 21

Trp Glu Val Ala His Gln Lys Leu Ala Cys Lys
1               5                   10


<210> SEQ ID NO 22
<211> LENGTH: 206
<212> TYPE: PRT
<213> ORGANISM: Homo sapiens

<400> SEQUENCE: 22

Glu Ala Arg Arg Thr Arg Lys Tyr Leu Glu Leu Tyr Ile Val Ala Asp
1               5                   10                  15

His Thr Leu Phe Leu Thr Arg His Arg Asn Leu Asn His Thr Lys Gln
            20                  25                  30

Arg Leu Leu Glu Val Ala Asn Tyr Val Asp Gln Leu Leu Arg Thr Leu
        35                  40                  45

Asp Ile Gln Val Ala Leu Thr Gly Leu Glu Val Trp Thr Glu Arg Asp
    50                  55                  60

Arg Ser Arg Val Thr Gln Asp Ala Asn Ala Thr Leu Trp Ala Phe Leu
65                  70                  75                  80

Gln Trp Arg Arg Gly Leu Trp Ala Gln Arg Pro His Asp Ser Ala Gln
                85                  90                  95

Leu Leu Thr Gly Arg Ala Phe Gln Gly Ala Thr Val Gly Leu Ala Pro
            100                 105                 110

Val Glu Gly Met Cys Arg Ala Glu Ser Ser Gly Gly Val Ser Thr Asp
        115                 120                 125

His Ser Glu Leu Pro Ile Gly Ala Ala Ala Thr Met Ala His Glu Ile
    130                 135                 140

Gly His Ser Leu Gly Leu Ser His Asp Pro Asp Gly Cys Cys Val Glu
145                 150                 155                 160

Ala Ala Ala Glu Ser Gly Gly Cys Val Met Ala Ala Ala Thr Gly His
                165                 170                 175

Pro Phe Pro Arg Val Phe Ser Ala Cys Ser Arg Arg Gln Leu Arg Ala
            180                 185                 190

Phe Phe Arg Lys Gly Gly Gly Ala Cys Leu Ser Asn Ala Pro
        195                 200                 205


<210> SEQ ID NO 23
<211> LENGTH: 8
<212> TYPE: PRT
<213> ORGANISM: Artificial
<220> FEATURE:
<223> OTHER INFORMATION: SG linker with a polyHis Tag
```

-continued

<400> SEQUENCE: 23

Ser Gly His His His His His His
1 5

<210> SEQ ID NO 24
<211> LENGTH: 1239
<212> TYPE: DNA
<213> ORGANISM: Homo sapiens
<220> FEATURE:
<221> NAME/KEY: misc_feature
<222> LOCATION: (1)..(54)
<223> OTHER INFORMATION: "pre" sequence
<220> FEATURE:
<221> NAME/KEY: misc_feature
<222> LOCATION: (55)..(78)
<223> OTHER INFORMATION: linker sequence
<220> FEATURE:
<221> NAME/KEY: misc_feature
<222> LOCATION: (79)..(597)
<223> OTHER INFORMATION: "prodomain"
<220> FEATURE:
<221> NAME/KEY: misc_feature
<222> LOCATION: (598)..(1215)
<223> OTHER INFORMATION: wild-type catalytic domain
<220> FEATURE:
<221> NAME/KEY: misc_feature
<222> LOCATION: (1216)..(1239)
<223> OTHER INFORMATION: SG linker with a polyHis Tag

<400> SEQUENCE: 24
atgaagttat gcatattact ggccgtcgtg gcctttgttg gcctctcgct cgggagatct 60
ccatggcccg ggtaccgct tcaaggacat atccctgggc agccagtcac cccgcactgg 120
gtcctggatg gacaaccctg gcgcaccgtc agcctggagg agccggtctc gaagccagac 180
atggggctgg tggccctgga ggctgaaggc caggagctcc tgcttgagct ggagaagaac 240
cacaggctgc tggccccagg atacatagaa acccactacg gcccagatgg gcagccagtg 300
gtgctggccc ccaaccacac ggatcattgc cactaccaag ggcgagtaag ggtttcccc 360 gactcctggg tagtcctctg cacctgctct gggatgagtg gcctgatcac cctcagcagg 420
aatgccagct attatctgcg tccctggcca ccccggggct ccaaggactt ctcaacccac 480
gagatctttc ggatggagca gctgctcacc tggaaaggaa cctgtggcca cagggatcct 540
gggaacaaag cgggcatgac cagtcttcct ggtggtcccc agagcagggg caggcgagaa 600
gcgcgcagga cccggaagta cctggaactg tacattgtgg cagaccacac cctgttcttg 660
actcggcacc gaaacttgaa ccacaccaaa cagcgtctcc tggaagtcgc caactacgtg 720
gaccagcttc tcaggactct ggacattcag gtggcgctga ccggcctgga ggtgtggacc 780
gagcgggacc gcagccgcgt cacgcaggac gccaacgcca cgctctgggc cttcctgcag 840
tggcgccggg ggctgtgggc gcagcggccc cacgactccg cgcagctgct cacgggccgc 900
gccttccagg gcgccacagt gggcctggcg cccgtcgagg gcatgtgccg cgccgagagc 960
tcgggaggcg tgagcacgga ccactcggag ctccccatcg gcgccgcagc caccatggcc 1020
catgagatcg gccacagcct cggcctcagc cacgaccccg acggctgctg cgtggaggct 1080
gcggccgagt ccggaggctg cgtcatggct gcggccaccg ggcacccgtt tccgcgcgtg 1140
ttcagcgcct gcagccgccg ccagctgcgc gccttcttcc gcaagggggg cggcgcttgc 1200
ctctccaatg ccccgtcagg acatcatcat caccatcat 1239

-continued

```
<210> SEQ ID NO 25
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: ADAM33 pre domain

<400> SEQUENCE: 25

Met Gly Trp Arg Pro Arg Arg Ala Arg Gly Thr Pro Leu Leu Leu Leu
1               5                   10                  15

Leu Leu Leu Leu Leu Leu Trp Pro Val Pro Gly Ala Gly Val Leu Gln
            20                  25                  30


<210> SEQ ID NO 26
<211> LENGTH: 18
<212> TYPE: PRT
<213> ORGANISM: Drosophila melanogaster
<220> FEATURE:
<221> NAME/KEY: MISC_FEATURE
<222> LOCATION: (1)..(18)
<223> OTHER INFORMATION: BIP pre domain

<400> SEQUENCE: 26

Met Lys Leu Cys Ile Leu Leu Ala Val Val Ala Phe Val Gly Leu Ser
1               5                   10                  15

Leu Gly


<210> SEQ ID NO 27
<211> LENGTH: 22
<212> TYPE: PRT
<213> ORGANISM: Drosophila melanogaster
<220> FEATURE:
<221> NAME/KEY: misc_feature
<222> LOCATION: (1)..(22)
<223> OTHER INFORMATION: PIPP pre domain

<400> SEQUENCE: 27

Met Lys Leu Thr Lys Leu Trp Leu Leu Phe Val Cys Leu Gly Leu Phe
1               5                   10                  15

Val Thr Leu Val Val Ser
            20


<210> SEQ ID NO 28
<211> LENGTH: 21
<212> TYPE: PRT
<213> ORGANISM: Apis mellifera
<220> FEATURE:
<221> NAME/KEY: MISC_FEATURE
<222> LOCATION: (1)..(21)
<223> OTHER INFORMATION: HBM pre domain

<400> SEQUENCE: 28

Met Lys Phe Leu Val Asn Val Asn Leu Val Phe Met Val Val Tyr Ile
1               5                   10                  15

Ser Tyr Ile Tyr Ala
            20


<210> SEQ ID NO 29
<211> LENGTH: 16
<212> TYPE: PRT
<213> ORGANISM: Tenebrio molitor
<220> FEATURE:
<221> NAME/KEY: MISC_FEATURE
<222> LOCATION: (1)..(16)
<223> OTHER INFORMATION: H1C pre domain
```

```
<400> SEQUENCE: 29

Met Tyr Lys Phe Val Val Phe Ala Ala Ala Leu Ala Tyr Ala Asn Ala
1               5                   10                  15


<210> SEQ ID NO 30
<211> LENGTH: 18
<212> TYPE: PRT
<213> ORGANISM: Aedes aegypti
<220> FEATURE:
<221> NAME/KEY: MISC_FEATURE
<222> LOCATION: (1)..(18)
<223> OTHER INFORMATION: LPM pre domain

<400> SEQUENCE: 30

Met Ala Met Leu Leu Gln Val Ala Leu Pro Leu Leu Ala Ala Val Ser
1               5                   10                  15

Trp Gly


<210> SEQ ID NO 31
<211> LENGTH: 18
<212> TYPE: PRT
<213> ORGANISM: Autographa californica nucleopolyhedrovirus
<220> FEATURE:
<221> NAME/KEY: MISC_FEATURE
<222> LOCATION: (1)..(18)
<223> OTHER INFORMATION: EGT pre domain

<400> SEQUENCE: 31

Met Thr Ile Leu Cys Trp Leu Ala Leu Leu Ser Thr Leu Thr Ala Val
1               5                   10                  15

Asn Ala


<210> SEQ ID NO 32
<211> LENGTH: 24
<212> TYPE: PRT
<213> ORGANISM: Autographa californica nucleopolyhedrovirus
<220> FEATURE:
<221> NAME/KEY: MISC_FEATURE
<222> LOCATION: (1)..(24)
<223> OTHER INFORMATION: P67 pre domain

<400> SEQUENCE: 32

Met Val Ser Ala Ile Val Leu Tyr Val Leu Leu Ala Ala Ala Ala His
1               5                   10                  15

Ser Ala Phe Ala Ala Glu His Cys
            20


<210> SEQ ID NO 33
<211> LENGTH: 413
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: “pre” sequence
<220> FEATURE:
<221> NAME/KEY: MISC_FEATURE
<222> LOCATION: (19)..(26)
<223> OTHER INFORMATION: linker sequence
<220> FEATURE:
<221> NAME/KEY: MISC_FEATURE
<222> LOCATION: (27)..(199)
<223> OTHER INFORMATION: “prodomain”
<220> FEATURE:
<221> NAME/KEY: MISC_FEATURE
<222> LOCATION: (200)..(405)
<223> OTHER INFORMATION: wild-type catalytic domain
```

```
<220> FEATURE:
<221> NAME/KEY: MISC_FEATURE
<222> LOCATION: (406)..(413)
<223> OTHER INFORMATION: SG linker with a polyHis Tag

<400> SEQUENCE: 33

Met Lys Leu Cys Ile Leu Leu Ala Val Val Ala Phe Val Gly Leu Ser
1               5                   10                  15

Leu Gly Arg Ser Pro Trp Pro Gly Val Pro Leu Gln Gly His Ile Pro
            20                  25                  30

Gly Gln Pro Val Thr Pro His Trp Val Leu Asp Gly Gln Pro Trp Arg
        35                  40                  45

Thr Val Ser Leu Glu Glu Pro Val Ser Lys Pro Asp Met Gly Leu Val
    50                  55                  60

Ala Leu Glu Ala Glu Gly Gln Glu Leu Leu Leu Glu Leu Glu Lys Asn
65                  70                  75                  80

His Arg Leu Leu Ala Pro Gly Tyr Ile Glu Thr His Tyr Gly Pro Asp
                85                  90                  95

Gly Gln Pro Val Val Leu Ala Pro Asn His Thr Asp His Cys His Tyr
            100                 105                 110

Gln Gly Arg Val Arg Gly Phe Pro Asp Ser Trp Val Val Leu Cys Thr
        115                 120                 125

Cys Ser Gly Met Ser Gly Leu Ile Thr Leu Ser Arg Asn Ala Ser Tyr
    130                 135                 140

Tyr Leu Arg Pro Trp Pro Pro Arg Gly Ser Lys Asp Phe Ser Thr His
145                 150                 155                 160

Glu Ile Phe Arg Met Glu Gln Leu Leu Thr Trp Lys Gly Thr Cys Gly
                165                 170                 175

His Arg Asp Pro Gly Asn Lys Ala Gly Met Thr Ser Leu Pro Gly Gly
            180                 185                 190

Pro Gln Ser Arg Gly Arg Arg Glu Ala Arg Arg Thr Arg Lys Tyr Leu
        195                 200                 205

Glu Leu Tyr Ile Val Ala Asp His Thr Leu Phe Leu Thr Arg His Arg
    210                 215                 220

Asn Leu Asn His Thr Lys Gln Arg Leu Leu Glu Val Ala Asn Tyr Val
225                 230                 235                 240

Asp Gln Leu Leu Arg Thr Leu Asp Ile Gln Val Ala Leu Thr Gly Leu
                245                 250                 255

Glu Val Trp Thr Glu Arg Asp Arg Ser Arg Val Thr Gln Asp Ala Asn
            260                 265                 270

Ala Thr Leu Trp Ala Phe Leu Gln Trp Arg Arg Gly Leu Trp Ala Gln
        275                 280                 285

Arg Pro His Asp Ser Ala Gln Leu Leu Thr Gly Arg Ala Phe Gln Gly
    290                 295                 300

Ala Thr Val Gly Leu Ala Pro Val Glu Gly Met Cys Arg Ala Glu Ser
305                 310                 315                 320

Ser Gly Gly Val Ser Thr Asp His Ser Glu Leu Pro Ile Gly Ala Ala
                325                 330                 335

Ala Thr Met Ala His Glu Ile Gly His Ser Leu Gly Leu Ser His Asp
            340                 345                 350

Pro Asp Gly Cys Cys Val Glu Ala Ala Ala Glu Ser Gly Gly Cys Val
        355                 360                 365

Met Ala Ala Ala Thr Gly His Pro Phe Pro Arg Val Phe Ser Ala Cys
    370                 375                 380
```

-continued

```
Ser Arg Arg Gln Leu Arg Ala Phe Phe Arg Lys Gly Gly Gly Ala Cys
385                 390                 395                 400

Leu Ser Asn Ala Pro Ser Gly His His His His His His
                405                 410


<210> SEQ ID NO 34
<211> LENGTH: 65
<212> TYPE: DNA
<213> ORGANISM: Artificial
<220> FEATURE:
<223> OTHER INFORMATION: PCR primer

<400> SEQUENCE: 34

atctgatatc tcgagtcaat gatggtgatg atgatgtcct gacggggcat tggagaggca     60

agcgc                                                                 65


<210> SEQ ID NO 35
<211> LENGTH: 43
<212> TYPE: DNA
<213> ORGANISM: Artificial
<220> FEATURE:
<223> OTHER INFORMATION: PCR primer

<400> SEQUENCE: 35

ttagattcat agggtaccgc ttcaaggaca tatccctggg cag                       43


<210> SEQ ID NO 36
<211> LENGTH: 28
<212> TYPE: PRT
<213> ORGANISM: Artificial
<220> FEATURE:
<223> OTHER INFORMATION: synthetic peptide

<400> SEQUENCE: 36

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25


<210> SEQ ID NO 37
<211> LENGTH: 8
<212> TYPE: PRT
<213> ORGANISM: Artificial
<220> FEATURE:
<223> OTHER INFORMATION: synthetic peptide

<400> SEQUENCE: 37

Glu Val Ala His Gln Lys Leu Ala
1               5


<210> SEQ ID NO 38
<211> LENGTH: 6
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION
```

-continued

```
<400> SEQUENCE: 38

Val Ala His Gln Lys Leu
1               5


<210> SEQ ID NO 39
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Biotin detectable moiety attached to N-terminus
<220> FEATURE:
<221> NAME/KEY: MOD_RES
<222> LOCATION: (11)..(11)
<223> OTHER INFORMATION: PHOSPHORYLATION of side chain

<400> SEQUENCE: 39

Tyr Glu Val His His Gln Lys Leu Val Phe Tyr
1               5                   10


<210> SEQ ID NO 40
<211> LENGTH: 11
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Biotin detectable moiety attached to N-terminus
<220> FEATURE:
<221> NAME/KEY: MOD_RES
<222> LOCATION: (11)..(11)
<223> OTHER INFORMATION: PHOSPHORYLATION of side chain
<220> FEATURE:
<221> NAME/KEY: MOD_RES
<222> LOCATION: (11)..(11)
<223> OTHER INFORMATION: AMIDATION

<400> SEQUENCE: 40

Trp Glu Val Ala His Gln Lys Leu Ala Lys Tyr
1               5                   10
```